United States Patent [19]
Strunk et al.

[11] Patent Number: 5,492,555
[45] Date of Patent: Feb. 20, 1996

[54] AUTOMATED TWO-DIMENSIONAL INTERFACE FOR CAPILLARY GAS CHROMATOGRAPHY

[75] Inventors: Michael R. Strunk; William E. Bechtold, both of Albuquerque, N.M.

[73] Assignee: Lovelace Biomedical & Environmental Research Institute, Inc., Albuquerque, N.M.

[21] Appl. No.: 257,388

[22] Filed: Jun. 9, 1994

[51] Int. Cl.$^6$ ................................................ B01D 15/08
[52] U.S. Cl. ........................... 95/86; 95/87; 96/104; 96/105; 96/106; 73/23.37; 73/23.41
[58] Field of Search .................... 83/23.35, 23.37, 83/23.41, 23.42; 95/82, 86, 87; 96/101, 104–106; 422/54, 89

[56] References Cited

U.S. PATENT DOCUMENTS

| | | | |
|---|---|---|---|
| 3,087,112 | 4/1963 | Pfefferle | 96/104 X |
| 3,518,059 | 6/1970 | Levy | 95/86 X |
| 3,524,305 | 8/1970 | Ives | 55/386 |
| 3,585,002 | 6/1971 | Boys | 95/86 X |
| 3,650,090 | 3/1972 | Temple et al. | 95/82 |
| 4,274,967 | 6/1981 | Snyder | 210/659 |
| 4,553,985 | 11/1985 | Dahlgren et al. | 95/82 X |
| 5,071,547 | 12/1991 | Cazer et al. | 210/198.2 |
| 5,083,450 | 1/1992 | Grindstaff | 73/23.25 |
| 5,135,549 | 8/1992 | Phillips et al. | 55/67 |
| 5,152,176 | 10/1992 | Bryselbout et al. | 95/86 X |
| 5,196,039 | 3/1993 | Phillips et al. | 95/86 X |
| 5,281,256 | 1/1994 | Sacks et al. | 95/86 |

OTHER PUBLICATIONS

K. Himberg et al., *Organohalogen Compd.*, vol. 4, Misc. Contr., 1989, pp. 183–186.
B. Gordon et al., *J. Chromatogr. Sci.*, vol. 23, No. 1, 1985, pp. 1–10.
G. Schomburg et al., *Chromatographia*, vol. 16, 1982, pp. 87–91.
D. J. Abbott, *J. High Resolut. Chromatogr., Chromatogr. Commun.*, vol. 7, No. 10, 1984, p. 577.
B. Wong, *J. Chromatogr.*, vol. 495, 1989, pp. 21–30.

*Primary Examiner*—Robert Spitzer
*Attorney, Agent, or Firm*—Roger F. Phillips

[57] ABSTRACT

A multidimensional gas chromatograph (GC) system having wide bore capillary and narrow bore capillary GC columns in series and having a novel system interface. Heart cuts from a high flow rate sample, separated by a wide bore GC column, are collected and directed to a narrow bore GC column with carrier gas injected at a lower flow compatible with a mass spectrometer. A bimodal six-way valve is connected with the wide bore GC column outlet and a bimodal four-way valve is connected with the narrow bore GC column inlet. A trapping and retaining circuit with a cold trap is connected with the six-way valve and a transfer circuit interconnects the two valves. The six-way valve is manipulated between first and second mode positions to collect analyte, and the four-way valve is manipulated between third and fourth mode positions to allow carrier gas to sweep analyte from a deactivated cold trap, through the transfer circuit, and then to the narrow bore GC capillary column for separation and subsequent analysis by a mass spectrometer. Rotary valves have substantially the same bore width as their associated columns to minimize flow irregularities and resulting sample peak deterioration. The rotary valves are heated separately from the GC columns to avoid temperature lag and resulting sample deterioration.

20 Claims, 3 Drawing Sheets

AUTOMATED TWO-DIMENSIONAL INTERFACE FOR CAPILLARY GAS CHROMATOGRAPHY

The United States Government has rights in this invention pursuant to Contract No. DE-AC04-76EV01013 between the Department of Energy and Lovelace Biomedical and Environmental Research Institute, Inc.

BACKGROUND OF THE INVENTION

1. Field of the Invention

The present invention relates to the field of gas chromatography. More particularly, the present invention relates to multi-dimensional gas chromatography and interfaces therefor.

2. Description of the Prior Art

Multidimensional gas chromatography is an analytical technique which further enhances the resolving power of single column gas chromatography. The term dimension, in the context of this technique, is defined as packed or capillary columns in a multiple column system, each column having differing selectivities based on their stationary phases. In general, two columns are connected in a manner that allows chromatographic separation on a primary column, followed by the introduction of regions of eluent or "heart cuts" from that column into a secondary column. The system which provides for the collection and manipulation of the heart cuts is known as the "system interface".

Three general design approaches for system interfaces have previously been employed in multi-dimensional gas chromatography. The use of rotary valves was developed as a column coupling mechanism as early as 1958 to separate $C_5$ through $C_7$ hydrocarbons on packed columns (see K. Himberg et al., *Organohalogen Compd.*, vol. 4, Misc. Contrl., 1989, pp. 183–186). Rotary valves are simple to use, however, two problems have been encountered with their use in system interfaces. First, switching valves have a large thermal mass. When temperature gradients are applied during gas chromatographic analysis, the switching valve temperature does not rise at the same rate as the rest of the chromatographic column (thermal lag). The resulting "cold spot" causes broadening of peaks and inconsistent retention times. Second, switching valves may have exposed metal surfaces that catalyze the reactive degradation of unstable analytes.

The limitations of existing rotary valves led to the development of the "Dean's switch" in 1968 (see B. Gordon et al., *J. Chromatogr. Sci.*, vol. 23, No. 1, 1985, pp. 1–10). The Dean's switch was the first attempt to enable live, valveless, multicolumn gas chromatography by placing a pneumatic switch between two columns in a series. This switching is possible only through the precise balance of carrier gas pressures at the inlet and at the column connection.

A third distinct approach to performing multidimensional chromatography has been the use of controlled temperature regions to generate "wave fronts" of sample on directly linked columns (thermal modulation). In this approach, units of column are treated with a resistive coating which is heated by applying a potential across it. The entire sample is therefore chromatographed on both columns successively (see U.S. Pat. No. 5,135,549 to Phillips et al. (1992)).

The Dean's switch, as used in present commercially available instruments or retrofit devices capable of performing multidimensional gas chromatography, is a pneumatically controlled interface system which uses slight differences in inlet and outlet pressure to cut windows of column eluent from a primary column to a secondary column. Essential to the operation of the Dean's switch is the use of a column coupling piece which directs flow from a primary column to either a monitor detector or an analytical column. Prior to the introduction of the "live T" (see G. Schomburg et al, *Chromatographia*, vol. 16, 1982, pp. 87–92), Dean's switch coupling components exhibited catalytic degradation of sample components. The predominant system used today, the Siemens Sinchromat 2 (Siemens AG, Karlsruhe, Germany), incorporates Schromburg's "live T". This coupling component is a six-port union which includes a platinum/iridium insert. Two ports serve to connect columns in a series, two ports connect to carrier gas flows, and two ports connect to detectors through flow restrictors. Solenoid valves, needle valves, and restrictors outside the direct column flow path are precisely adjusted and switched to cut eluent from the first column onto the second. Difficulties encountered in Dean's switch operation are generally due to the nature of trying to control minute pressure differences while varying column temperature. Column flow rate is inversely proportional to temperature, and pressure is directly proportional to temperature. To resolve these difficulties, Abbott attempted to direct pre- and post-column flows (peripheral to the coupling piece) with mass flow controllers (see D. J. Abbott, *J. High Resolut. Chromatogr., Chromatogr, Commun.*, vol. 7, No. 10, 1984, p. 577). Because of slower equilibrium times associated with the controllers, narrow cuts from the primary column could not be obtained.

Single or multiple stage thermal modulation is a process that involves the cooling and heating of regions of chromatography columns coupled in series. Cooling of a discrete region of a column causes sample to be focused onto a narrow band. A rapid increase in temperature drives that band off as a wave. This accumulation, transfer, and release of sample between temperature controlled regions of a column allows small portions of a complete sample to be sequentially introduced onto the second column in series. Multiple stage thermal modulation involves creation of several thermally controlled regions of column, normally near both the inlet and the outlet of each column. Heating of regions of column has been accomplished by treating them with a resistive coating and applying a voltage across the resistance (see U.S. Pat. No. 5,135,549 to Phillips, above).

The most pronounced advantage of thermal modulation is the ability to chromatograph an entire sample on both a primary and a secondary column. Disadvantages include the fact that detectors which are easily contaminated suffer insult from everything introduced on column. Also, because thermal modulation alone doesn't allow coupling of mismatched column diameters or the flexibility to make multiple injections, trace enrichment is not possible on the system design. Elaborate temperature programming is necessary to manage narrow bands of sample. Finally, an instrument modified for thermal modulation is a dedicated instrument which does not allow the flexibility of using either column independently.

Mechanical valve coupling of multiple columns is the most direct and simple means of multidimensional gas chromatography (See Gordon, above). Column flows are set as they would be in one dimensional analysis. Because sample flows are directed through low voltage paths in rotary valves, flexibility in design and use are maintained. Non-dedicated instruments can be maintained to allow an operator the option of either one-dimensional analysis or two-dimensional analysis without major reassembly of the instrument.

Rotary valve system interfaces initially suffered from two primary drawbacks. The valves exhibit a large thermal mass due to their bulky nature, and, prior to the advent of micro valves, large metal surface areas within the valves served as sites of activity (acidity, adsorption, or poor efficiency). Minimized activity and reduction of thermal lag in rotary valves was accomplished by using a valve which was independently heated, and had flow paths equivalent in diameter to its attached capillary column.

Several rotary valve system interface design variations have been used to accomplish the task of GC column coupling. The most common approach is the use of a single six port bimodal valve which mimics the path configuration of the "live T". However, with a rotary valve, no pressure balancing is necessary with columns of identical diameter and length. Wong employed a combination of four port and six port bimodal rotary valves in a system interface in the multidimensional analysis of d-arabinitol in serum (see B. Wond, *J. Chromatrogr.*, vol. 495, 1989, pp. 21–30).

It is desirable in many analyses to interface capillary GC columns having substantially different bore sizes. This enables large volume samples to be injected and separated with ultimate high component resolution and sensitivity. Large injection volumes of hundreds of microliters can routinely be made on wide bore capillary columns (typically about 0.53 mm I.D.). In contrast, even with the new pressure pulsed injection techniques being used today, injection volumes of only 5 to 10 microliter can be made onto the narrow bore GC columns (typically from 0.18 to 0.25 mm internal diameter). In the case of a GC configured to a mass spectrometer, column flow rates of only about 1 ml/min. of carrier gas can be accommodated in the vacuum chamber of the detector. This limits the GC selection to only narrow bore capillary. Therefore, only small injection volumes can be made onto the GC/MS making the detection limits of a given method a function of only the sample preparation, and the instrument detection limit. Existing system interfaces do not have the capability to interface such wide bore/narrow bore GC systems effectively.

The present invention overcomes several problems encountered in the prior art including cold spots due to the large thermal mass of rotary valves, the requirement to dedicate an instrument solely to two-dimensional analysis, and the lack of isolated cold traps, while providing a two-dimensional wide bore-narrow bore chromatography system capable of convenient use. The inventive system provides a dedicated oven for maintaining the rotary valves at an elevated temperature, thereby eliminating thermal lag in temperature programmed chromatographic analysis. Column flow adjustments are made at the column inlets eliminating the need for delicate pressure adjustment as required in present Dean's switch systems. The provision in the present inventive system interface of a heartcut trap isolated from any carrier gas flows allows for easy maintenance of cold trap equilibrium and minimized sample breakthrough.

The advantages of the present invention can be illustrated by a comparison with the Wong device (see above). The Wong system interface features mechanical valve heads contained within the same oven as the chromatography column. As temperature programs are executed, valve temperatures lag behind column temperatures because of the large thermal mass of the valve bodies. Cold spots are created within the valves which disrupt chromatography. A four port valve serves to direct primary column flow to either a monitor/detector or a cold trap (liquid $CO_2$). The second valve, a six port valve, serves to direct flow from the cold trap to the analytical column/detector. Because of the narrow internal diameter of the paths in the valves (0.25 mm), and because any flow from the primary column must flow through both valves, the use of two columns of drastically different internal diameters is not possible without changing the configuration or balancing flows with restrictors. If multiple analytes are to be trapped, possible losses may occur during the chromatographic run as carrier gas is constantly flowing through the cold trap. In comparison, the inventive system and system interface employs a bimodal six port valve having an internal diameter comparable to the primary column from which it directs flow. All separation/cleanup and trapping of sample components is accomplished while avoiding the directing of flow through the second valve (a small internal diameter bimodal four port valve). This enables the use of columns with very different internal diameters to be coupled without adjusting flows or pressures to compensate. The second valve of the present invention is comparable in inside diameter to the small bore analytical column for which it directs flow. A second carrier gas inlet source allows either direct access to the analytical column or to the cold trap. Valve bodies and cold trap are kept in a separate oven at elevated temperatures, eliminating thermal lag effects. The inventive flow configuration allows any trapped analytes to be completely isolated from carrier gas flow until the desired analysis time.

Column flow in a gas chromatographic system is determined by several variables: column length, internal diameter (including any additional restriction within the flow path), column head pressure, stationary phase and carrier composition, and thermal expansion during temperature programming. In the inventive configuration, each column is completely isolated from its series counterpart during all portions of an analysis. In addition, no restriction is introduced into the path of either valve which would reduce the flow during any portion of an analysis, even when valves are rotated for peak capture, etc. This allows flows for diverse capacity columns to be set and maintained independently without affecting the flow of the other column. A further consideration is that, using valve internal diameters which are too large increases inefficiently swept flow system volumes (dead volumes). As pointed out by Jennings (see W. Jennings, *J. Chromatogr. Sci.*, vol. 22, 1984, pp. 129–135) minimizing internal diameter of mechanical valve paths diminishes degradation of sample components within the valves. In the inventive design, each valve path is minimized to accommodate its corresponding column without unduly restricting flow to the complimentary column. In contrast to the inventive design, a prior art design such as that of Wong, above, which limits valve diameter during all switching steps, will disrupt system flow, necessitating the coupling of identical or nearly identical columns through the minimized diameter valve flow paths.

The present invention, then, provides for optimum sample flows in a multidimensional gas GC system employing significantly differing column bore widths, consistent with economical system interface design, while avoiding the difficult pressure balancing procedures or sample deterioration of prior art systems.

SUMMARY OF THE INVENTION

The present invention provides a novel system interface for carrying out multidimensional gas chromatography (GC) which allows the use of GC columns such as capillary GC columns having significantly differing bore sizes and thus requiring mismatched carrier gas flow rates. Such a system is desirable where large sample sizes are processed while final GC carrier gas flow rates must be small to accommodate mass detectors such as mass spectrometers.

It is an object of this invention to provide a multidimensional gas chromatograph system (MGCS) capable of operation with multiple GC columns having significantly differing bore diameters.

It is another object of this invention to provide a MGCS capable of operation with mismatched carrier gas flow rates.

It is yet another object of this invention to provide a MGCS capable of operation without the use of complex GC heating regimes.

It is yet another object of the present invention to provide a MGCS capable of processing large initial sample sizes with multiple components while providing for highly defined final analysis with mass detectors such as a mass spectrometer.

It is yet another object of this invention to provide a MGCS interface having a sample trap capable of isolation from carrier gas flows.

It is yet another object of the invention to provide a MGCS interface wherein fine adjustment of gas pressures and flow rates is not required in its operation.

It is yet another object of the invention to provide a MGCS interface with independently heated switching valves which avoid temperature leg resulting in sample peak degradation.

It is yet another object of the present invention to provide a MGCS interface having individual switching valves comparable in internal diameter to the individual GC columns with which they are associated.

It is yet another object of the present invention to provide a MGCS interface which allows for single dimension analysis without significant reconfiguration of the system.

Additional objects, advantages, and novel features of the invention will become apparent to those skilled in the art upon examination of the following description or may be learned by practice of the invention. The objects and advantages of the invention may be realized and attained by means of the instrumentalities and combinations particularly pointed out in the appended claims.

To achieve the foregoing and other objects, and in accordance with the purpose of the present invention, as embodied and broadly described herein, the present invention may comprise a multidimensional gas chromatograph (GC) system for separating a multicomponent sample into its components and detecting said components, said system having a wide bore GC column, a narrow bore GC column, and an interface for directing at least a portion of the eluant from said wide bore GC column to said narrow bore GC column, the improvement wherein said system having eluant switching means operatively connected with an outlet of said wide bore GC column, final analyte switching means operatively connected with an inlet of said narrow bore GC column, and eluant trapping and retaining means located between and operatively connecting said eluant switching means and said final analyte switching means, said eluant trapping and retaining means being so configured as to be capable of flow isolation from each of said wide bore and said narrow bore GC columns by said eluant and said final analyte switching means whereby said eluant switching means is operable to direct selected portions of the eluant from said wide bore GC column to said trapping and retaining means to form a final analyte and said final analyte switching means is operable to direct said final analyte to said narrow bore GC column.

BRIEF DESCRIPTION OF THE DRAWINGS

The accompanying drawings, which are incorporated in and form part of the specification, illustrate an embodiment of the present invention and, together with the description, serve to explain the principles of the invention.

DETAILED DESCRIPTION OF THE INVENTION

The present invention allows the interface of two different capillary Gas Chromatograph (GC) columns which require mismatched carrier gas flow rates. This enables large volume samples to be injected and separated on two individual capillary columns with enhanced component resolution and method sensitivity.

It is known that large injection volumes of hundreds of microliters can routinely be made on wide bore capillary columns (0.53 mm I.D.). In contrast, even with the new pressure pulsed injection techniques being used today, injection volumes of only 5 to 10 microliter can be made onto the narrow bore (0.18 mm to 0.25 mm internal diameter) GC columns. In the case of a GC configured to a mass spectrometer (MS), column flow rates of only about 1 ml/min. of carrier gas can be accommodated in the vacuum chamber of the detector. This limits the column selection to only narrow bore capillary columns. Therefore, only small injection volumes can be made onto the GC/MS making the detection limits of a given method a function of only the sample preparation, and the instrument detection limit.

As sample load onto a column increases, the resolving power of the capillary column decreases, being more evident as the sample matrix overwhelms any trace components of the mixture. This is due in part to the absolute capacity of a capillary column. Therefore, only a portion of the total initial sample injected onto the wide-bore column can be effectively analyzed on the narrow bore capillary column.

The interface system of the present invention takes advantage of the rugged sample handling capacity of a wide bore capillary column (large injection capacity, large sample loading capacity, and its potential as a pre-analysis sample clean-up column), while maintaining the necessary low flow rates to the mass spectrometer through a narrow bore capillary column, ultimately increasing method limits of detection because of the increased sample load.

Figure 1:
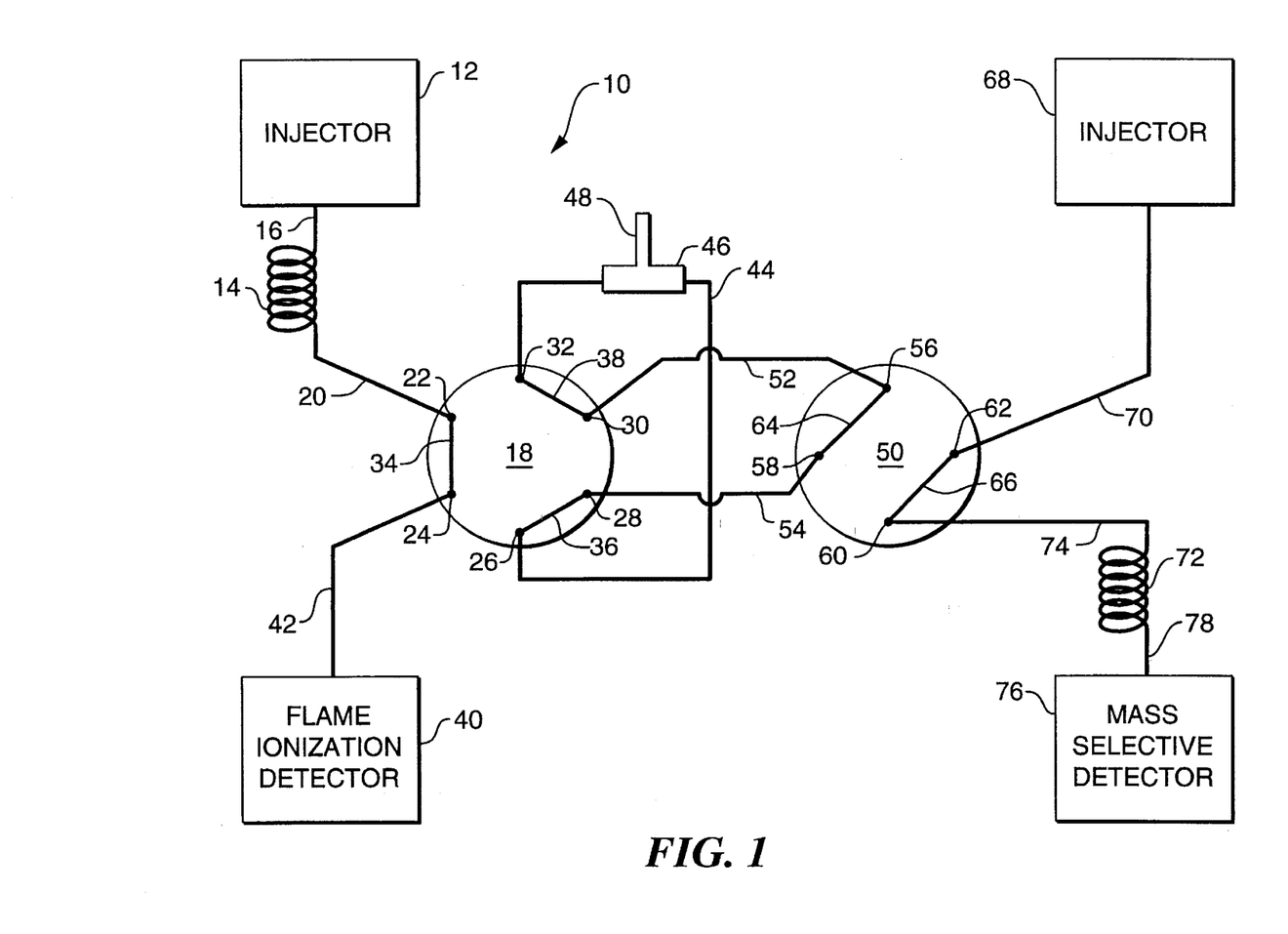
FIG. 1 is a flow diagram representing the MGCS of the present invention with the system interface in either the sample injection mode or the peak isolation mode.
Figure 2:
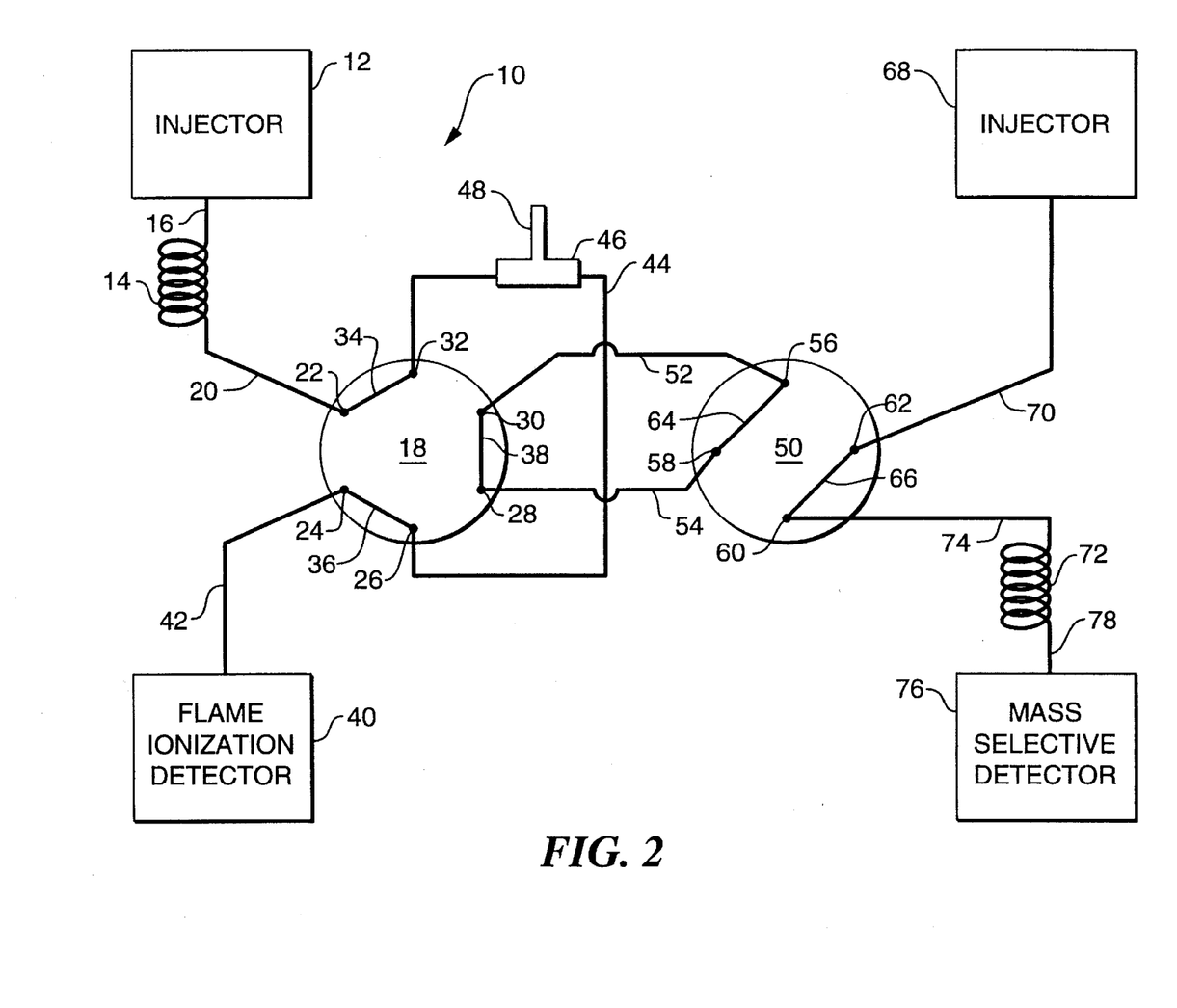
FIG. 2 is a flow diagram representing the MGCS of the present invention with the system interface in the component peak capture mode.
Figure 3:
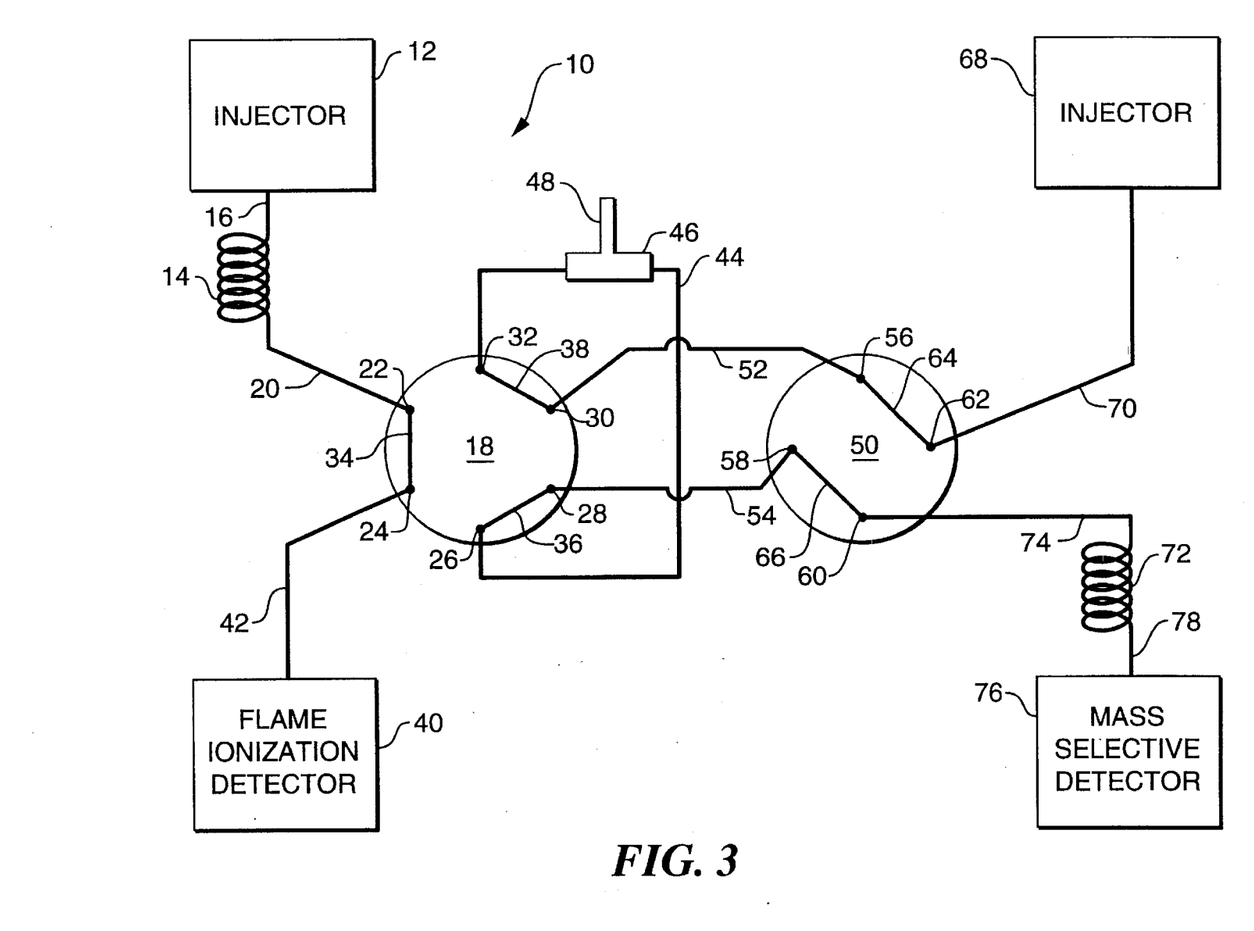
FIG. 3 is a flow diagram representing the MGCS of the present invention with the system interface in the GC/MS reinjection mode.

Referring to FIGS. 1, 2, and 3, GC/MS system 10 is shown in the raw sample injection mode (see FIG. 1) wherein first sample injection system 12 is connected with large bore capillary column 14 by means of first injection line 16. Six-way valve 18 is connected to large bore capillary column 14 by means of large bore capillary column exit line 20. Bimodal six-way valve 18 contains first six-way valve port 22, second six-way valve port 24, third six-way valve port 26, fourth six-way valve port 28, fifth six-way valve port 30 and sixth six-way valve port 32. Six-way valve 18 further contains first six-way valve passage 34, second six-way valve passage 36, and third six-way valve passage 38. First six-way valve port 22 is connected with wide bore capillary column exit line 20. First detector 40 is connected with six-way valve 18 by means of first detector feed line 42 at second six-way valve port 24.

Sample collection or trapping circuit 44 is connected with six-way valve 18 at third six-way valve port 26 and sixth six-way valve port 32 and includes sample cryofocusser 46 having cryogenic fluid inlet 48. Bimodal four-way valve 50 is connected with six-way valve 18 by means of first intervalve analyte transfer line 52 at first four-way valve port 56 and fifth six-way valve port 30, respectively, and by means of second intervalve analyte transfer line 54 at second four-way valve port 58 and fourth six-way valve port 28. Four-way valve 50 further includes third four-way valve port 60 and fourth four-way valve port 62, and first four-way valve passage 64 and second four-way valve passage 66. Second injection system 68 is connected to four-way valve 50 by means of second injection line 70 connected at fourth four-way valve port 62.

Narrow bore capillary column 72 is connected to four-way valve 50 by means of narrow bore capillary column feed line 74 connected at third four-way valve port 60. Second detector 76 is connected with the narrow bore capillary column 72 by means of second detector feed line 78. All connections in the above-described system are operable connections for fluid flow.

In operation, in the sample injection mode (See FIG. 1) sample and carrier gas are injected by first injection system 12 to large bore capillary column 14 through first injection line 16 at a relatively high flow rate in the range of 5 to 20 mL/min., where the sample is separated into a series of individual component composition peaks. The resulting gas stream is transported to six-way valve 18 by means of large capillary column exit line 20 and first six-way valve port 22. The column eluant gas stream is initially directed to first detector 40 by means of first six-way valve passage 34, second six-way valve port 24, and first detector feed line 42. Observation of first detector 40, which may be a flame ionization or other type of detector, indicates when individual sample component peaks are leaving large capillary column 14. Concentrated samples of desired sample components may be collected from these composition peaks and captured by manipulation of six-way valve 18 to the peak capture position (See FIG. 2) for appropriate periods of time while maintaining valve 18 in the sample injection mode during non-peak periods as determined by first detector 40. Appropriate times for switching valve 18 may also be predetermined by the injection of individual standard compositions and the recording of the time required for components to emerge from wide bore column 14. The resulting concentrated sample is trapped in sample collection of trapping circuit 44 by means of sample cryofocusser 46 during the above-described sample collecting manipulations of valve 18. In the peak isolation mode of the invention (See FIG. 1) six-way valve 18 and four-way valve 50 are in the same positions as in the sample injection mode, but the concentrated sample is now isolated in a trapping, retaining, and transfer circuit defined by sample collection or trapping circuit 44, first intervalve analyte transfer line 52, and second intervalve analyte transfer line 54, line 52 interconnecting with collection circuit 44 through third six-way valve passage 38 by means of fifth six-way valve port 30 and sixth six-way valve port 32, and line 54 interconnecting with collection circuit 44 through second six-way valve passage 36 by means of fourth six-way valve port 28 and third six-way valve port 26. Intervalve lines 52 and 54 are connected at four-way valve 50 in its sample collection/peak capture/peak isolation position (See FIGS. 1 and 2) by means of first four-way valve passage 64 and four-way valve ports 56 and 58, respectively, thus forming a closed reservoir for the previously isolated sample compositional peaks.

When all analytes have been cryofocused, the GC oven (not shown) is cooled to ambient or subambient temperatures and the system is reconfigured to the GC/MS reinjection mode by manipulating four-way valve 50. During the GC/MS reinjection mode (See FIG. 3) coolant flow to the inventive system is discontinued to cryofocusser 48, allowing rapid desorption of captured analytes, therein, and four-way valve 50 is manipulated to the reinjection position, allowing carrier gas from second injector 68 to flow through second injection line 70 to first intervalve analyte transfer line 52 by means of fourth four-way valve port 62, first four-way valve passage 64, and first four-way valve port 56. Carrier gas then travels to sample collection or trapping circuit 44 through fifth six-way valve port 30, third six-way valve passage 38, and sixth six-way valve port 32, where it mixes with the collected sample peak composition previously isolated. The peak sample mixture then flows into second intervalve analyte transfer line 54 through third six-way valve port 26, second six-way valve passage 36, and fourth six-way valve port 28. The peak sample mixture then flows to narrow bore capillary column 72 through second four-way valve port 58, second four-way valve passage 66, third four-way valve port 60 and small bore capillary column feed line 74. Because the narrow bore capillary column has been cooled, the analytes refocus at the head of the column. The GC oven (not shown) temperature of the narrow bore capillary column is increased for elution of the analytes. These analytes are then carried into narrow bore capillary column 72 where they are separated into concentration peaks which then flow through second detector feed line 78 to second detector 76, which is preferably a mass selective detector such as a mass spectrometer where final analysis is carried out. Carrier gas flow rate is adjusted at second injector 68 to maintain flow through small bore capillary column 72 at less than 1 mL/min. An oven (not shown) maintains the temperature of valves 18 and 50 independent of the GC oven.

The invention is illustrated by the following example:

EXAMPLE 1

Quantification of the levels of 1,3-butadiene (BD), butadiene monoxide (BDO), and butadiene diepoxide ($BDO_2$) in blood was carried out as part of a study to determine the roles of metabolism and dose in species differences (rats vs. mice) in the toxicity of BD. Tissue distillates were analyzed using multidimensional GC/MS, according to the present invention. Metabolites isolated from blood by vacuum distillation were condensed into a cold trap. After warming the traps to room temperature, BD and BDO were sampled from the trap vapor phase. $BDO_2$ was extracted from the co-distilled water phase using ethyl acetate. Samples were analyzed using a multidimensional GC system equipped with the interface of the present invention. Approximately 0.75 mL of blood from control or exposed animals was added to 50 mL round-bottomed flasks. These flasks had been stoppered, evacuated, and tared immediately prior to use. An internal standard solution of BDO—$D_6$ and $BDO_2$—$d_6$ was added, aliquots of diluted BD—$d_6$ gas were added using a gas-tight syringe, and the contents were well mixed and frozen on liquid nitrogen.

The volatile BD metabolite were isolated from nonvolatile impurities by vacuum-line distillation. A 10-port manifold was evacuated with a two-stage vacuum pump to below 0.01 Torr. Contents of the 50 mL round-bottomed flask were distilled through a 10-mL U-tube modified with a sampling port (septaport U-traps). The septaport U-traps were held at −196° C. by liquid nitrogen. Blood samples in the round-bottomed flasks were distilled until visually dry.

The contents of the traps were analyzed for BD, BDO, and BDO$_2$ using the BD/BD/MS apparatus of the present invention. Preliminary experiments showed that BD and BDO partitioned significantly into the septaport U-trap headspace, while BDO$_2$ remained in the water that had co-distilled. BD and BDO were measured from the headspace of the septaport U-traps held at room temperature. Headspace (2–10 mL) from the septaport U-trap was removed with a glass syringe and injected directly onto the first column.

At the initial GC oven temperature (50° C.), little retention of BD or BDO occurred on the first column. Therefore, after injection of headspace, the first 2 min. of eluant were directed to the cryofocusser (See FIG. 2). After the two analytes had eluted, the six-port switching valve was rotated (See FIG. 3), thereby precluding the transfer of water vapor to the cryofocusser. The four-port valve was then rotated, the cryofocusser was turned off, and the analytes were transferred to the second column. The GC oven temperature was increased to 250° C. at 10° C./min. The BD and BDO peaks eluted at 10.0 and 12.9 min., respectively.

The MS was operated in the selected ion mode. Ions that were monitored for BD, BDO, BD—d$_6$, and BDO—d$_6$ are shown in Table 1. Peaks were integrated, and ion ratios were calculated to both internal standards and to each of the other ions from the same analyte. The former set of ion ratios was used for quantitation, while the latter set was used for confirmation of analyte identity. Standard curves were created by adding graded amounts of analyte to septaport U-traps with a consistent amount of water and internal standard, followed by analysis as described above.

The aqueous phase remaining in the septaport U-trap was removed for analysis of the BDO$_2$. The aqueous phase was extracted three times with separate 2 mL aliquots of ethyl acetate, and the organic phases were pooled. The organic extract was transferred to 2-mL autosampler vials and reduced in volume to between 50 and 100 microliter by passing a stream of nitrogen gas over the sample at room temperature.

The organic extract was analyzed for BDO$_2$ by GC/GC/MS according to the present invention by using the same columns described above. Injections of up to 10 microliter indicated that peak areas were linear with injection volume. For convenience, 5 microliter of the extract were injected. Initially, the switching valves directed eluate to the flame ionization detector (See FIG. 1). The initial oven temperature was 50° C. for 2.5 min., followed by an increase of 15° C./min. to 150° C. The oven was held at this temperature for 1 min. BDO$_2$ was shown to have a retention time of 7.0 min. under these conditions. Therefore, at 6.5 min., the six-port valve was rotated to direct column eluate to the prechilled cryofocusser (See FIG. 2). This process effectively excluded any solvent. At 7.5 min., the six-port valve was rotated back to the original position (See FIG. 1). After completion of the oven temperature gradient, the oven was cooled to 25° C. and held for 5 min. The cryofocusser was turned off at 16 min. and the four-port valve rotated at 16.5 min. to transfer the BDO$_2$ to the second column. The oven temperature was increased at 15° C./min. to 150° C. and held at this temperature for 4.5 min. The BDO$_2$ peak eluted at 23.4 min. under these conditions. The ions monitored for BDO$_2$ and BDO$_2$—d$_6$ are shown in Table 1.

TABLE 1

Assignment of Ions for Quantitation and Confirmation of BD and Metabolites

| Analyte | Analyte Ions | Deuterated Internal Standard Ions |
|---|---|---|
| BD | 39, 54 | 42, 60 |
| BDO | 39, 41, 69 | 46, 74 |
| BDO$_2$ | 29, 55 | 30, 58 |

Although a variety of components may be used in the inventive configuration, the components employed in the Example 1 system were a Hewlett Packard 5890 Gas Chromatograph and a Hewlett Packard 5970 Mass Selective Detector employing a Hewlett Packard UX Data station (Hewlett Packard, North Hollywood, Calif.) The valves employed were Valco six- and four-port mechanical switching valves housed in an oven separate from that of the BD (Valco, Houston, Tex.). The transfer line between the two switching valves was Restek deactivated fused silica (Restek, Bellefonte, Pa.), 0.53 mm id which passes through a cryogenic focusser of SGE glassware. The large bore capillary column was an Alltech At-Wax capillary column (Allteck, San Jose, Calif.), 15 m× 0.54 mm ID, with a 2.5 micrometer film thickness. The small bore capillary column was a Restek RT$_x$-200 capillary column, 30 m× 0.25 mm ID, with a 0.25 micrometer film thickness. Other system line sizes were selected to match the column diameter with which they were most closely associated. The valve oven is maintained at an elevated temperature (250° C.) by the use of valve heaters. Temperatures in the oven were controlled by using thermocouples. All timed events for the switching valves and the cryofocusser were controlled by use of a Nelson Analytical station (P. E. Nelson, Norwalk, Connecticut).

The particular sizes and equipment discussed above are cited merely to illustrate a particular embodiment of this invention. It is contemplated that the use of the invention may involve components having different sizes and shapes as long as the principles, the provision of a multidimensional GC interface providing for heartcut trap isolation from carrier gas flows for ease of cold trap equilibrium and minimized sample breakthrough, the provision of flow system component sizes matching their associated GC columns to avoid sample degradation, and the provision of switching valves heated separately from GC columns to avoid thermal lag, are followed. It is intended that the scope of the invention be defined by the claims appended hereto.

We claim:

1. In a multidimensional gas chromatograph (GC) system for separating a multicomponent sample into its components and detecting said components, said system having a wide bore GC column, a narrow bore GC column, and an interface for directing at least a portion of an eluant from said wide bore GC column to said narrow bore GC column, the improvement wherein said system having eluant switching means operatively connected with an outlet of said wide bore GC column, final analyte switching means operatively connected with an inlet of said narrow bore GC column, and eluant trapping and retaining means located between and operatively connecting said eluant switching means and said final analyte switching means, said eluant trapping and retaining means being so configured as to be capable of flow isolation from each of said wide bore and said narrow bore GC columns by said eluant and said final analyte switching means whereby said eluant switching means is operable to direct selected portions of the eluant from said wide bore GC column to said trapping and retaining means to form a final analyte and said final analyte switching means is operable to direct said final analyte to said narrow bore GC column.

2. The multidimensional GC system of claim 1 wherein said wide bore GC column is a capillary column and said narrow bore GC column is a capillary column.

3. The multidimensional GC system of claim 2, said trapping and retaining means further comprising a cold trap for trapping and separating analyte from the effluent from said wide bore GC column.

4. The multidimensional GC system of claim 3 further comprising first detector means operatively connected with said eluant switching means for detecting components of the eluant from said wide bore GC column.

5. The multidimensional GC system of claim 4 further comprising first injector means for injecting said sample into said wide bore GC column.

6. The multidimensional GC system of claim 4 wherein said trapping and retaining means further comprises a trapping circuit connected with said eluant switching means, and an analyte transfer circuit connecting said eluant switching means and said final analyte switching means.

7. The multidimensional GC system of claim 6 wherein said eluant switching means is a bimodal six-way valve alternately connecting in a first position said wide bore GC column with said first detector means and said trapping circuit with said transfer circuit and in a second position said wide bore GC with said trapping circuit.

8. The multidimensional GC system of claim 7 wherein said six-way valve has internal passage substantially equal in bore width to said wide bore GC column.

9. The multidimensional GC system of claim 7 further comprising a second injector operatively connected with said final analyte switching means for injecting carrier gas into said analyte transfer circuit.

10. The multidimensional GC system of claim 9 wherein said final analyte switching means is a bimodal four-way valve alternately isolating in a first position said transfer circuit from said second injector and said narrow bore GC column and in a second position connecting in turn said second injector, said transfer circuit and said narrow bore GC column.

11. The multidimensional GC system of claim 10 wherein said four-way valve has internal passages substantially equal in bore width to said narrow bore GC column.

12. The multidimensional GC system of claim 10 wherein said cold trap is switchable between an active state and an inactive state whereby upon inactivation of said cold trap analytes are converted to gaseous form and upon positioning said final analyte valve in said second position said analytes are swept from said connector circuit by said carrier gas into said narrow bore GC for separation and analysis.

13. The multidimensional system of claim 12 further comprising a second detector connected to an outlet of said narrow bore GC.

14. The multidimensional GC system of claim 13 wherein said second detector is a mass spectrometer.

15. The multidimensional GC system of claim 14 wherein said first detector is a flame ionization detector.

16. The multidimensional GC system of claim 15 wherein said six-way valve and said four-way valve are pneumatically controlled.

17. The multidimensional GC system of claim 16 wherein said four-way valve and said six-way valve have independently controlled heating means.

18. The multidimensional GC system of claim 17 wherein said four-way valve and said six-way valve are located in a common oven.

19. A method of operating a multidimensional GC system having a wide bore GC column, a narrow bore GC column, a mass spectrometer, and an interface for transferring selected portions of an eluate from said wide bore GC column to said narrow bore GC column, said interface having a bimodal six-way eluate switching valve and an analyte trapping and retaining circuit operatively connected therewith, a bimodal four-way final analyte switching valve operatively connected with said narrow bore GC column and a second injector, and a transfer circuit operatively connected with said eluate six-way switching valve and said final analyte four-way switching valve comprising the steps of:

(A) positioning said six-way valve in a first position and said four-way valve in a first position;

(B) injecting a sample into said wide bore GC column at a first flow rate such that the eluate travels through said six-way valve to a first detector;

(C) switching said six-way valve to a second position at such times and for such time intervals as to route desired components from the eluate to said trapping and retaining circuit for collecting and retaining in a cold trap mounted therein;

(D) positioning said six-way valve in said second position to isolate said trapping and retaining circuit, and deactivating said cold trap to vaporize a final analyte trapped therein;

(E) repositioning said four-way valve to a second position;

(F) injecting a carrier gas from said second injector at a second flow rate substantially lower than said first flow rate into said trapping reservoir and sweeping said analyte to said narrow bore GC column; and (G) directing a resulting eluate to said mass spectrometer compatible with said second flow rate.

20. A multidimensional gas chromatograph system comprising:

(A) a wide bore capillary GC column having an inlet and an outlet;

(B) a first injector connected with said wide bore capillary GC column inlet for injecting sample into said wide bore GC column;

(C) a bimodal six-way valve connected with said wide bore capillary GC column outlet;

(D) a flame ionization detector connected with said six-way valve;

(E) a trapping and retaining circuit connected with said six-way valve;

(F) a cold trap located in said trapping and retaining circuit;

(G) a bimodal four-way valve;

(H) a transfer circuit connecting said six-way valve and said four-way valve;

(I) a second injector connected with said four-way valve; and (J) a narrow bore GC column having an inlet and an outlet connected with a mass spectrometer which is in turn connected with said four-way valve;

(K) said six-way valve operatively connecting for fluid flow in a first position said wide bore GC with said flame ionization detector and said trapping and retaining circuit with said transfer circuit, and in a second position said GC column with said trapping and retaining circuit and said flame ionization circuit, while isolating said transfer circuit;

(L) said four-way valve in a first position isolating said transfer circuit and operatively connecting for fluid flow said second injector and said narrow bore GC column, and in a second position connecting said second injector with said transfer circuit and said transfer circuit with said narrow bore GC column;

(M) said six-way valve having internal passages substantially equal in bore width to said wide bore GC column and said four-way valve having internal passages substantially equal in bore width to said narrow-bore GC column;

(N) said second injector being operable to inject carrier gas at a flow rate compatible with said mass spectrometer, and said first injector being operable for introducing sample to said wide bore GC column at a flow rate substantially higher than the flow rate of carrier gas from said second injector.

* * * * *